United States Patent [19]
Moje

[11] 4,042,373
[45] Aug. 16, 1977

[54] 2-ARYL-3-CHLORO-2,4,6,7-TETRAHYDRO-THIOPYRANO[4,3-C]-PYRAZOLES
[75] Inventor: Steven William Moje, Newark, Del.
[73] Assignee: E. I. Du Pont de Nemours and Company, Wilmington, Del.
[21] Appl. No.: 692,052
[22] Filed: June 2, 1976
[51] Int. Cl.² ............... A01N 9/14; C07D 495/04
[52] U.S. Cl. ............................................. 71/91; 71/90; 71/92; 548/370
[58] Field of Search ............................ 71/92, 91, 90; 260/310 R

[56] References Cited
U.S. PATENT DOCUMENTS

| | | | |
|---|---|---|---|
| 3,235,564 | 2/1966 | Wagner | 71/91 |
| 3,590,049 | 6/1971 | Swett et al. | 260/310 R |
| 3,883,550 | 5/1975 | Goddard | 71/92 |

OTHER PUBLICATIONS
Chemical Abstracts, vol. 84 : 4845m (1976).

Primary Examiner—Donald B. Moyer

[57] ABSTRACT
Compounds of the formula

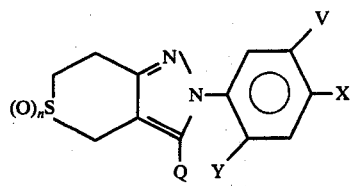

(I)

where
  $n$ is 0, 1, or 2;
  Q is chlorine or bromine;
  X is fluorine, chlorine, bromine, or cyano;
  Y is hydrogen, fluorine, or chlorine; and
  V is hydrogen, fluorine, chlorine or alkoxy of 1 to 3 carbon atoms.

25 Claims, No Drawings

2-ARYL-3-CHLORO-2,4,6,7-TETRAHYDROTHIOPYRANO[4,3-c]-PYRAZOLES

BACKGROUND OF THE INVENTION

Recently, in German Offenlegungsschrift No. 2,165,651 a group of isoindole-1,3-diones which are useful as herbicides was disclosed. The general formula for the isoindole-1,3-diones disclosed in the Offenlegungsschrift is as follows:

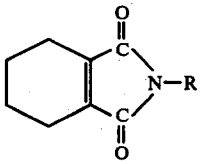

wherein R may be an aryl, aralkyl or benzyl optionally substituted with 1 to 5 halogen atoms, hydroxy, nitro, cyano, thiocyanato, carboxy, alkyl or halogenated alkyl, alkoxy, lower alkylthio, and phenyl groupings; a group having the configuration —O—Ch$_2$A may also be substituted therein, wherein A is a phenyl or a naphthyl group, wherein the phenyl group may have one or more substituents therein, such as halogen atoms, nitro groupings, lower alkyl groupings or lower alkoxy groupings.

Typical of the compounds disclosed in the Offenlegungsschrift is the compound of Example 1:

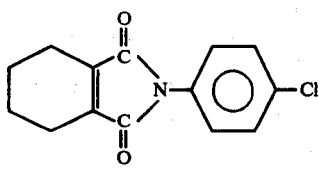

Although the compounds disclosed within the Offenlegungsschrift are active herbicides, the need still exists for herbicides which are more active. The presence of undesired vegetation is very damaging to useful crops such as rice and wheat. In the current world situation, wherein food shortages are acute, it is most important not to lose a portion of a valuable crop such as rice or wheat. The presence of such undesired vegetation results in the loss of a significant portion of such crops. Thus, a need exists for a particularly effective herbicide which will destroy as much of this unwanted vegetation as is possible without causing significant damage to the desired crops, e.g. rice.

According to the instant invention, herbicidal compounds have been discovered which are highly active herbicides and yet cause minimal damage to certain desired crops, e.g. rice and wheat.

DESCRIPTION OF THE INVENTION

This invention relates to novel compounds of Formula 1, to agricultural compositions containing such compounds, and to the method of use of these compounds as herbicides, both for general control of undesired vegetation and for specific control of barnyardgrass in rice. The sulfides and sulfoxides are useful intermediates to the more herbicidally active sulfones.

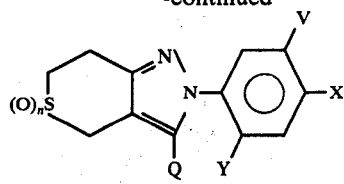

where
n is 0, 1 or 2;
Q is chlorine or bromine;
X is fluorine, chlorine, bromine, or cyano;
Y is hydrogen, fluorine, or chlorine; and
V is hydrogen, fluorine, chlorine, or alkoxy of 1 to 3 carbon atoms.

The sulfides and sulfoxides (n = 0 or 1) serve as useful intermediates to the more herbicidally active sulfones of Formula 1 where independently
a. n is 2; and
b. Q is chlorine; or
c. Y is fluorine; or
d. V is hydrogen; or
e. X is chlorine, bromine or fluorine.

Specifically preferred for their outstanding herbicidal activity are:
a. 3-Chloro-2-(4-chloro-2-fluorophenyl)-2,4,6,7-tetrahydrothiopyrano[4,3-c]pyrazole-5,5-dioxide, m.p. 141°–144° C;
b. 3-Chloro-2-(4-bromo-2-fluorophenyl)-2,4,6,7-tetrahydrothiopyrano[4,3-c]pyrazole-5,5-dioxide.

SYNTHESIS OF THE COMPOUNDS

The compounds of this invention are prepared by condensation and ring closure of the appropriate aryl hydrazine 3 and β-keto ester 2, followed by reaction with phosphorous oxyhalide, POQ$_3$, and oxidation, as shown in Equation A:

(A)

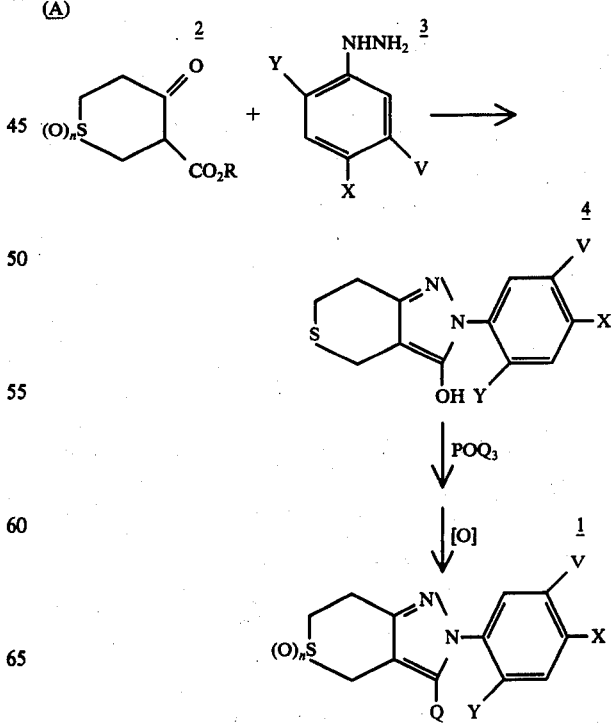

The preparation of the ketocarboalkoxythiopyrone 2 is known in the literature; for example, the preparation of 3-carbomethoxytetrahydro-1,4-thiopyrone from β,β'-dimethyl thiodipropionate and sodium methoxide in ether is described by E. A. Fehnel and M. Carmack in *J. Amer. Chem. Soc.* 70, 1813 (1948).

The thiopyrone 2 is combined with the appropriate aryl hydrazine 3 and an optional acidic catalyst, such as acetic acid, in an appropriate solvent, such as toluene or other aromatic hydrocarbons, or lower alcohols and heated at reflux for 0.5–24 hours. Evolved water is removed to give the thiopyranopyrazole 4, which can be isolated by conventional techniques such as cooling the reaction mixture and filtering precipitated product or by evaporating the solvent at reduced pressure.

The novel thiopyranopyrazoles of Formula 1 are obtained by heating the thiopyranopyrazoles 4 with phosphorous oxychloride or phosphorous oxybromide. In the case of phosphorous oxybromide it is advantageous to use an equivalent of an N,N-dialkylaniline such as N,N-diethylaniline or use phosphorous oxybromide without added base in an inert solvent such as xylene.

Phosphorous oxychloride may be used as described above, however, it is preferred that no solvent other than phosphorous oxychloride be used.

The halogenating mixture is heated at 100°–180° C, preferably 140–150; for a period of 1–10 hours. The crude reaction mixture is dissolved in an inert organic solvent (e.g., CHCl$_3$, CH$_2$Cl$_2$, or toluene) and a weak base (e.g., saturated aqueous NaHCO$_3$) or dilute aqueous base (e.g., NaOH, KOH) is added. After thorough mixing, the phases are separated and the organic solvent phase is washed with weak base or dilute aqueous base. After a second washing with saturated aqueous NaCl or water, the organic phase is dried and the solvent removed on a rotary evaporator by distillation. The product obtained is a thiopyranopyrazole of Formula 1 and may be purified by crystallization from an appropriate solvent.

The thiopyranopyrazoles of Formula 1 may be oxidized to the corresponding solfoxides ($n=1$) or sulfones ($n=2$) by reaction with oxidizing reagents such as hydrogen peroxide, peracids, nitric acid, chromic acid, potassium permanganate, and sodium metaperiodate. Typical oxidations are described by G. Hilgetag and A. Martin in "Preparative Organic Chemistry", Wiley, 1972, pp 667–669, and by E. A. Fehnel and M. Carmack in *J. Amer. Chem. Soc.* 70, 1813 (1948), and in *Chem. Abstracts* 71: 80555p (1969).

Compounds of Formula 1 were $n = 1$ are prepared by slow dropwise addition of one equivalent of an oxidizing agent such as m-chloroperoxybenzoic acid or peroxyacetic acid to a compound of Formula 1 where $n = 0$ in a suitable inert organic solvent such as chloroform. This reaction is usually carried out at 0° 1 to 50° C for a period of 10 minutes to 24 hours. The product is isolated by removing the spent oxidizing agent by filtration or neutralization with an appropriate base such as sodium hydroxide and evaporating the solvent. If necessary, further purification can be accomplished by recrystallization, sublimation or other conventional techniques.

Compounds of Formula 1 where $n = 2$ are prepared as described above using two or more equivalents of the oxidizing agent.

The preparation of aryl hydrazines from aniles is well documented in the literature: G. H. Coleman, *Organic Syntheses, Coll. Vol. I*, J. Wiley & Sons, New York, p. 442 and H. Kindler, et al., Fr. 1,419,092. The general procedure is illustrated in Equation B:

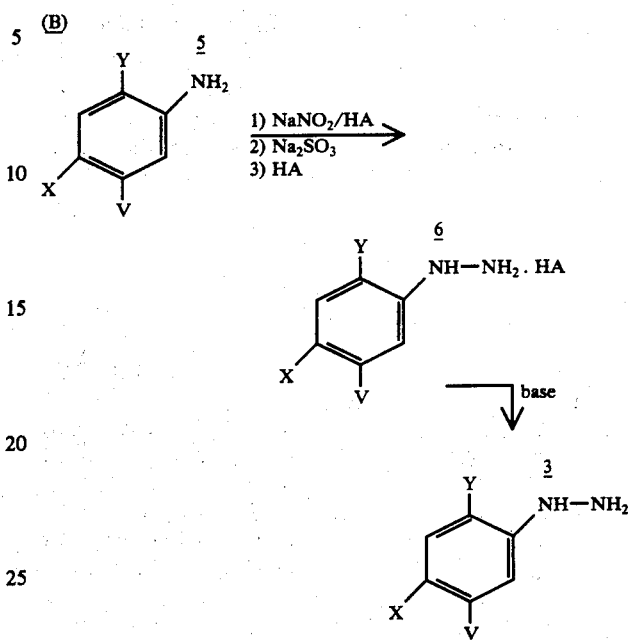

The aniline 5 is diazotized about −5° to 5° C with sodium nitrite in aqueous acid (HA, where A is defined as an anion of the corresponding acid HA having an ionization constant of at least $1 \times 10^{-7}$, e.g. H$_2$SO$_4$ or HCl) such as hydrochloric acid. The resulting solution is mixed with an aqueous sodium bisulite solution at 0°–20° C, heated to 50°–80° C for 0.5–2 hours and then acidified with the mineral acid to give the aryl hydrazine acid salt 6. The hydrazine salt often crystallizes directly from the reaction mixture and can be isolated by filtration or by other conventional techniques.

The aryl hydrazine acid salt 6 can be converted to the free hydrazine 3 by briefly shaking a suspension of 6 in a suitable organic solvent (e.g., CH$_2$Cl$_2$, CHCl$_3$ or toluene) and aqueous base (e.g., NaOH or KOH) until most or all of the acid salt 6 has dissolved. The organic phase is washed with water, dried and evaporated at reduced pressure to give the hydrazine 3. In most instances, the hydrazine can be used without further purification.

Certain of the hydrazines used in preparing the compounds defined by this invention are novel; e.g. 4-chloro-2-fluorophenylhydrazine is a novel compound which can be prepared by the method described above.

Alternatively, aryl hydrazines can be prepared by reduction of diazonium salts with stannous chloride as taught by M. S. Gibson et al. in *J. Chem. Soc. C,* 2108 (1974) and *J. Chem. Soc. Perkin I* 217 (1974). This method works well for the preparation of 4-bromo-2-fluorophenylhydrazine.

The aniline starting materials for these hydrazines are prepared as described below. 4-Chloro-2-fluoroaniline, for example, can be prepared from 2'-fluoroacetanilide [G. Schiemann and H. G. Baumgarten, *Chem. Berichte* 70, 1416 (1937)] by the reaction sequence shown below:

Step A

-continued

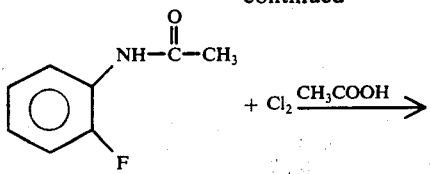
+ Cl$_2$ $\xrightarrow{CH_3COOH}$

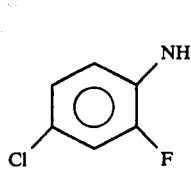

Step B

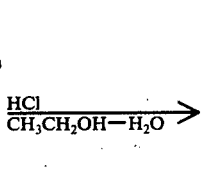
$\xrightarrow{HCl}{CH_3CH_2OH-H_2O}$

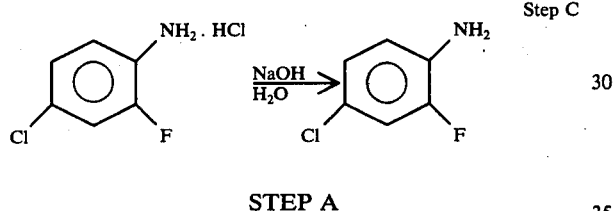

Step C

STEP A

The chlorination of acetanilides in acetic acid is well known to those skilled in the art and may be carried out under the conditions taught in W. W. Reed and K. J. P. Orton, *J. Chem. Soc.*, 91, 1543 (1907) for the chlorination of acetanilide. The chlorination of 2'-fluoroacetanilide takes place at 25°–30° C over several hours (e.g. A) at atmospheric pressure. The resulting product is 4'-chloro-2'-fluoroacetanilide.

STEP B

The chlorofluoroacetanilide is refluxed in a mixture of a lower alcohol (50%) (e.g. ethanol) and concentrated hydrochloric acid (50%) for several hours (e.g. 5 or more) at 70°–90° C an atmospheric pressure. The solvent mixture is removed at a reduced pressure of 100 to 300 mm Hg. and at a temperature of 20°–50° C to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution, such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm Hg. at 20°–50° C.

2-Fluoro-4-bromoaniline can be prepared by bromination of 2-fluoroaniline [prepared in Chem. Berichte, 70, 1416 (1937)] with N-bromosuccinimide as shown in the following equation.

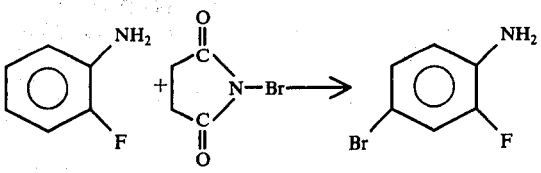

The bromination of anilines using N-bromosuccinimide in an inert organic solvent such as methylene chloride is well known to those skilled in the art, e.g., J. B. Wommack et al., *J. Het. Chem.* 6, 243 (1969). The bromination of 2-fluoroaniline is an exothermic reaction that takes place at 0° C over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under a reduced pressure of 100 to 300 mm Hg. at 20°–50° C.

The following examples further illustrate the method for synthesis of compounds of this invention. All parts are by weight and all temperatures in degrees centigrade.

EXAMPLE 1

Preparation of 3-Chloro-2-(4-chloro-2-fluorophenyl)-2,4,6,7-tetrahydro-thiopyrano[4,3-c]pyrazole

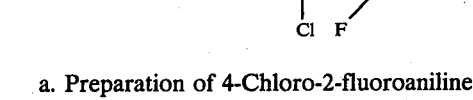

a. Preparation of 4-Chloro-2-fluoroaniline

Seventy-one parts of liquid chlorine were added to a solution of 140 parts of 2'-fluoroacetanilide in 500 parts glacial acetic acid, during an hour, at 25°–27° C, with ice-water cooling. While stirring for 4 hours at 25°–27° C, 4'-chloro-2'-fluoroacetanilide precipitated. After collecting the product by filtration, the filtrate was poured over 2000 parts of ice. The resulting second portion of precipitated product was collected by filtration, combined with the first portion and recrystallized from 7000 parts of methanol at −45° C to yield 119 parts of 4'-chloro-2'-fluoroacetanilide as white crystals melting at 152°–155° C.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm Hg. to yield the moist, solid hydrochloride salt of 4-chloro-2-fluoroaniline.

The moist, solid hydrochloride salt of 4-chloro-2-fluoroaniline was cooled to 10° C in an ice-acetone bath and 50% aqueous sodium hydroxide was added dropwise, with stirring, until pH 11 was obtained. The resulting two-phase mixture was extracted four times; 500 parts of methylene chloride was used for each extraction. The combined organic extracts were dried with anhydrous sodium sulfate and the solvent removed under a reduced pressure of 300 mm Hg. to leave 89 parts of light brown, oily 4-chloro-2-fluoroaniline, $n_D^{25} = 1.5541$.

b. Preparation of 4-Choro-2-fluorophenylhydrazine

200 Parts of 4-chloro-2-fluoroaniline was dissolved in 80 parts of water and 34 parts of concentrated hydrochloric acid. The solution was cooled to 0°–10° C and 32.2 parts of 30% sodium nitrite was added dropwise maintaining the temperature of the reaction between 0°–10° C. After the addition of nitrite was completed, the solution was stirred for 30 minutes at 0°–10° C. The excess nitrite was destroyed by the addition of small amounts of sulfamic acid. When a negative test with sulfone reagent was obtained, the diazonium salt was ready for reduction. For a description see H. E. Fierz-David et al., *Fundamental Processes of Dye Chemistry* translated from 5th Austrian Ed. by P. W. Wittam, Interscience Publishers, Inc., New York, 1949, p. 243.

In a separate vessel 35.4 parts of sodium bisulfite and 32.2 parts of 30% sodium hydroxide solution were dissolved in 140 parts of water. The solution was heated to 40° C. The diazonium salt was added to the bisulfite solution over a period of about 1 hour. The mixture was heated to 70° C and .03 parts of sodium bisulfite was added. The pH was adjusted to 1.2 with 30 parts of concentrated hydrochloric acid; then an additional 90 parts of concentrated hydrochloric acid was added. The reaction mixture was heated for 1.5 hours at 70° C, cooled slowly, and stirred overnight at room temperature.

Purification was achieved by heating the reaction mixture to 70° C and filtering. The filtrate was cooled to 10° C at which time the 4-chloro-2-fluorophenylhydrazine hydrochloride precipitated. This product was filtered and dried to yield 10.7 parts of yellow crystalline solid, m.p. 223° C.

Six parts of 4-chloro-2-fluorophenyl hydrazine hydrochloride was shaken with 100 parts of methylene chloride and 100 parts of 1-molar aqueous sodium hydroxide for one to two minutes until a clear two-phase solution was obtained. The organic phase was washed three times with 60 parts of water, dried with anhydrous magnesium sulfate, and evaporated under a reduced pressure of 50 to 300 mm Hg. to give 3.8 parts of pale tan 4-chloro-2-fluorophenyl hydrazine, m.p. 57°–63° C.

c. Preparation of 3-Chloro-2-(4-chloro-2-fluorophenyl)-2,4,6,7-tetrahydro-thiopyrano[4,3-c]pyrazole 8.0 Parts of 4-chloro-2-fluorophenyl hydrazine was reacted with 8.7 parts of 3-carbomethoxytetrahydro-1,4-thiopyrone in 150 parts of toluene and 0.1 part of acetic acid at 110° C for 12 hours. The reaction mixture was cooled to 25° C, and 11.1 parts of 3-hydroxy-2-(4-chloro-2-fluorophenyl)-2,4,6,7-tetrahydro-thiopyrano[4,3-c]pyrazole was collected by filtration as fine white needles, m.p. 206°–208° C.

12.4 Parts of 3-hydroxy-2-(4-chloro-2-fluorophenyl)-2,4,6,7-tetrahydro-thiopyrano[4,3-c]pyrazole was reacted with 6.7 parts of phosphorus oxychloride at 155° C for 3 hours, the reaction mixture poured into 250 parts of chloroform and 250 parts of saturated aqueous NaHCO$_3$ and stirred for 16 hours. The aqueous portion was extracted with 200 parts of chloroform, the chloroform portions combined and washed twice with 200 parts of water, dried with anhydrous magnesium sulfate, and evaporated under a reduced pressure of 50 to 300 mm Hg. to give 6.0 parts of 3-chloro-2-(4-chloro-2-fluorophenyl)-2,4,6,7-tetrahydro-thiopyrano[4,3-c]pyrazole as a black-brown oil which when contacted with a mixture of ether and pentane changed into a light brown solid, m.p. 97°–99° C.

Crystallization of this solid from ethanol gave crystals with m.p. 101°–101½° C.

EXAMPLE 2

Preparation of 3-Chloro-2-(4-chloro-2-fluorophenyl)-2,4,6,7-tetrahydrothiopyrano[4,3-c]pyrazole-5-oxide

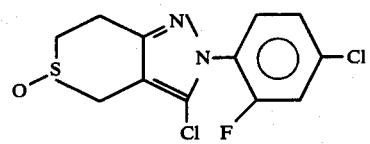

1.6 parts of 85% m-chloroperbenzoic acid dissolved in 110 parts of chloroform were added dropwise for 1 hour to a stirred solution of 3-chloro-2-(4-chloro-2-fluorophenyl)-2,4,6,7-tetrahydro-thiopyrano[4,3-c]pyrazole dissolved in 75 parts of chloroform. The resulting solution was stirred 16 hours, washed 4 times with 40 parts of saturated aqueous NaHCO$_3$, 2 times with water, dried with anhydrous magnesium sulfate, and solvent evaporated under a reduced pressure of 50 to 300 mm Hg. to give a pale yellow oil. The oil, when contacted with a mixture of ether and pentane, gave 1.2 parts of 3-chloro-2-(4-chloro-2-fluorophenyl)-2,4,6,7-tetrahydro-thiopyrano[4,3-c]pyrazole-5-oxide as a pale caramel-colored solid, m.p. 119°–122° C. This solid can be recrystallized from a mixture of methylene chloride, ether, and pentane to give m.p. 122½°–125° C.

EXAMPLE 3

Preparation of 3-Chloro-2-(4-chloro-2-fluorophenyl)-2,4,6,7-tetrahydrothiopyrano[4,3-c]pyrazole-5,5-dioxide

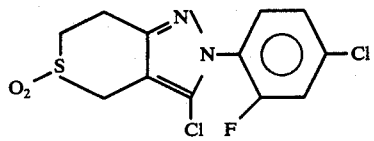

3.0 Parts of 3-chloro-2-(4-chloro-2-fluorophenyl)-2,4,6,7-tetrahydrothiopyrano[4,3-c]pyrazole was reacted with 4.1 parts of 85% m-chloroperbenzoic acid in 75 parts of chloroform with ice bath cooling to maintain the reaction temperature at 25° C. The reaction mixture was filtered after 12 hours to remove a white solid, this solid rinsed with 5 parts of chloroform, the chloroform portions washed twice with 200 parts of saturated aqueous NaHCO$_3$, twice with 20 parts of saturated aqueous sodium chloride, dried with anhydrous magnesium sulfate, and evaporated at a reduced pressure of 50 to 300 mm Hg. to give 1.5 parts of 3-chloro-2-(4-chloro-2-fluorophenyl)-2,4,6,7-tetrahydro-thiopyrano[4,3-c]pyrazole-5,5-dioxide as an orange semisolid. The product was recrystallized from ethanol and subsequently from 1-chlorobutane to give a pale yellow tan solid, m.p. 141°–143° C.

EXAMPLE 4 a.
3-Bromo-2-(4-chlorophenyl)-2,4,6,7-tetrahydrothiopyrano-[4,3-c]pyrazole-5,5-dioxide

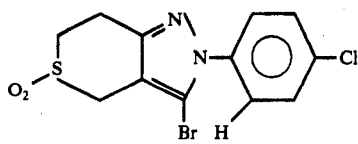

A mixture of 10.6 parts of 2-(4-chlorophenyl)-3-hydroxy-2,4,6,7-tetrahydro-thiopyrano[4,3-c]pyrazole, prepared according to the method of Example 1, and 12 parts of phosphorous oxybromide in 120 parts of xylene was refluxed for 7 hours and then stirred at room temperature for 12 hours. The suspension was neutralized with 5% sodium bicarbonate followed by extraction with chloroform (3 × 100 parts). The chloroform solution was washed with a saturated NaCl solution, dried over anhydrous magnesium sulfate and evaporated at a reduced pressure of 50 to 300 mm Hg, yielding a brown oil. This oil crystallized from acetone yielding 4.3 parts of the desired product, m.p. 138°–145° C; a second recrystallization from acetone/methylene chloride gave 3.4 parts of pure 3-bromo-2-(4-chlorophenyl)-2,4,6,7-tetrahydrothiopyrano[4,3-c]pyrazole, m.p. 143.5°–145° C.

b. Oxidation of 3-bromo-2-(4-chlorophenyl)-2,4,6,7-tetrahydrothiopyrano[4,3-c]pyrazole according to the method of Example 2 gives 3-bromo-2-(4-chlorophenyl)-2,4,6,7-tetrahydrothiopyrano[4,3-c]pyrazole-5-oxide.

c. Oxidation of 3-bromo-2-(4-chlorophenyl)-2,4,6,7-tetrahydrothiopyrano[4,3-c]pyrazole according to the method of Example 3 gives 3-bromo-2-(4-chlorophenyl)-2,4,6,7-tetrahydrothiopyrano[4,3-c]pyrazole-5,5-dioxide, m.p. 168.5°–169.5° C.

Using the procedure of Examples 1, 2, 3 and 4, the following compounds of Formula 1 can be prepared:

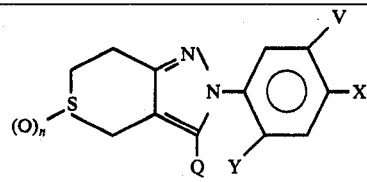

| n | Q | Y | X | V | m.p. ° C |
|---|---|---|---|---|----------|
| 0 | Cl | H | Cl | H | 89–91 |
| 0 | Cl | F | Br | H | |
| 0 | Cl | H | F | H | |
| 0 | Cl | H | Br | H | |
| 0 | Cl | H | CN | H | |
| 0 | Cl | Cl | Cl | H | |
| 0 | Cl | Cl | Cl | Cl | |
| 0 | Cl | F | F | F | |
| 0 | Cl | Cl | Cl | CH$_3$O | |
| 0 | Cl | Cl | Cl | (CH$_3$)$_2$CHO | |
| 0 | Br | F | Cl | H | |
| 0 | Br | H | CN | H | |
| 0 | Br | F | Br | H | |
| 1 | Cl | H | Cl | H | |
| 1 | Cl | F | Br | H | |
| 1 | Cl | H | F | H | |
| 1 | Cl | H | Br | H | |
| 1 | Cl | H | CN | H | |
| 1 | Cl | Cl | Cl | H | |
| 1 | Cl | Cl | Cl | Cl | |
| 1 | Cl | F | F | F | |
| 1 | Cl | Cl | Cl | CH$_3$O | |
| 1 | Cl | Cl | Cl | (CH$_3$)$_2$CHO | |

-continued

| n | Q | Y | X | V | m.p. ° C |
|---|---|---|---|---|----------|
| 1 | Br | F | Cl | H | |
| 1 | Br | H | CN | H | |
| 1 | Br | F | Br | H | |
| 2 | Cl | H | Cl | H | |
| 2 | Cl | F | Br | H | |
| 2 | Cl | H | F | H | |
| 2 | Cl | H | Br | H | |
| 2 | Cl | H | CN | H | |
| 2 | Cl | Cl | Cl | H | |
| 2 | Cl | Cl | Cl | Cl | |
| 2 | Cl | F | F | F | |
| 2 | Cl | Cl | Cl | CH$_3$O | |
| 2 | Cl | Cl | Cl | (CH$_3$)$_2$CHO | |
| 2 | Br | F | Cl | H | |
| 2 | Br | H | CN | H | |
| 2 | Br | F | Br | H | |

Useful formulations of the compounds of Formula 1 can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 0.25% to 99% by weight of active ingredient(s) and at least one of (a) about 0.1% to 20% surfactant(s) and (b) about 1% to 99.75% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 5–90 | 1–94 | 1–10 |
| Oil Suspensions, Emulsions, Solutions (including Emulsifiable Concentrates) | 5–50 | 40–95 | 0–15 |
| Aqueous Suspensions | 5–50 | 40–94 | 1–20 |
| Dusts | 0.25–25 | 70–99.75 | 0–5 |
| Granules and Pellets | 0.25–95 | 1–99.75 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N. J. The more absorptive diluents are preferred for wettable powders and the denser ones for dusts. Typical liquid diluents and solvents are described in Marsden, "Solvents Guide", 2nd Edn,. Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encylcopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Enginerring,* Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn., Blackwell Scientific Publications, Oxford, 1968, pp. 101–103.

In the following examples all parts are by weight and all temperatures in degrees centigrade unless otherwise indicated.

EXAMPLE 5

| Low Strength Granule | |
|---|---|
| 3-chloro-2-(4-chloro-2-fluorophenyl)-2,4,6,7-tetrahydrothiopyrano[4,3-c]pyrazole-5,5-dioxide | 0.5% |
| attapulgite granules (low volatile matter, 0.59–0.25 mm; USS 30–60 mesh size) | 99.5% |

Forty grams of a solution containing 2.5% 3-chloro-2-(4-chloro-2-fluorophenyl)-2,4,6,7-tetrahydrothiopyrano[4,3-c]pyrazole-5,5-dixoide is dissolved in methyl alcohol and slowly atomized onto a fluidized bed of attapulgite granules (199 g). Fluidization of the granules is continued after atomization is complete and until all the methyl alcohol is evaporated from the granules. The granules are packaged for use.

EXAMPLE 6

| High Strength Concentrate | |
|---|---|
| 3-chloro-2-(4-bromo-2-fluorophenyl)-2,4,6,7-tetrahydrothiopyrano[4,3-c]pyrazole-5,5-dioxide | 99% |
| trimethylnonyl polyethylene glycol ether | 1% |

The surfactant is sprayed upon the active ingredient in a blender and the mixture is sifted through a U.S.S. N. 40 sieve (0.42 mm openings) prior to packaging. The concentrate may be formulated further for practical use.

EXAMPLE 7

| Emulsifiable Concentrate | |
|---|---|
| 3-chloro-2-(4-chloro-2-fluorophenyl)-2,4,6,7-tetrahydrothiopyrano[4,3-c]pyrazole-5,5-dioxide | 20% |
| blend of oil soluble sulfonates and polyoxyethylene ethers | 4% |
| xylene | 76% |

The ingredients are combined and stirred until solution is complete. A fine screen filter is included in the packaging operation to insure the absence of any extraneous undissolved material in the product.

EXAMPLE 8

| Solution | |
|---|---|
| 3-chloro-2-(4-chloro-2-fluorophenyl)-2,4,6,7-tetrahydrothiopyrano[4,3-c]pyrazole-5,5-dioxide | 20% |
| dimethylformamide | 80% |

The ingredients are stirred to produce a solution, which can be used for low-volume applications.

EXAMPLE 9

| Granule | |
|---|---|
| 3-chloro-2-(4-bromo-2-fluorophenyl)-2,4,6,7-tetrahydrothiopyrano[4,3-c]pyrazole-5,5-dioxide | 10% |
| attapulgite granules (low volatile matter, 0.71–0.30 mm; U.S.S. #25–50 sieves) | 90% |

The active ingredient is dissolved in acetone and sprayed onto dedusted, tumbling granules in a double cone blender. The acetone is removed by evaporation and recovered. The acetone-free granules are then packaged.

EXAMPLE 10

| Extruded Pellet | |
|---|---|
| 3-chloro-2-(4-chloro-2-fluorophenyl)-2,4,6,7-tetrahydrothiopyrano[4,3-c]pyrazole-5,5-dioxide | 25% |
| anhydrous sodium sulfate | 10% |
| crude calcium ligninsulfonate | 5% |
| sodium alkylnaphthenesulfonate | 1% |
| calcium/magnesium bentonite | 59% |

The ingredients are blended, hammer milled and then moistened with about 12% water. The mixture is extruded as cyclinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Aqueous Suspension | |
|---|---|
| 3-chloro-2-(4-bromo-2-fluorophenyl)-2,4,6,7-tetrahydrothiopyrano[4,3-c]pyrazole-5,5-dioxide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 12

| Wettable Powder | |
|---|---|
| 3-Chloro-2(4-chloro-2-fluorophenyl)-2,4,6,7-tetrahydrothiopyrano[4,3-c]pyrazole-5,5-dioxide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. N. 50 sieve (0.3 mm opening) before packaging.

EXAMPLE 13

| Granule | |
|---|---|
| 3-chloro-2-(4-bromo-2-fluorophenyl)-2,4,6,7-tetrahydrothiopyrano[4,3-c]pyrazole-5,5-dioxide | 2% |
| dimethylformamide | 10% |
| attapulgite granules (low volatile matter, 9.71–0.30 mm; U.S.S. #25–50 mesh sieves) | 88% |

Four grams of 3-chloro-2-(4-bromo-2-fluorophenyl)-2,4,6,7-tetrahydrothiopyrana[4,3-c]pyrazole 5,5-dioxide are dissolved in 20 g of dimethylformamide. This solution is sprayed onto a tumbling bed of 176 g of attapulgite granules. The granules are packaged in a container with a vapor barrier to prevent loss of dimethylformamide.

Compositions can contain, in addition to the active ingredients of this invention, other conventional agricultural chemicals such as fertilizers, plant growth modifiers or herbicides.

For example, the compounds of Formula I can be combined with other herbicides and are particularly useful in combination with bromacil [3-(sec-butyl)-5-bromo-6-methyluracil], diuron[3-(3,4-dichlorophenyl)-1,1-dimethylurea], 3-cyclohexyl-1-methyl-6-dimethylamino-s-triazine-2,4-(1H,3H)-dione, paraquat[1,1'-dimethyl-4,4'-bipyridinium ion], m-(3,3-dimethylureido)-phenyl tert-butylcarbamate, 2-methyl-4-chlorophenoxyacetic acid, its salts or esters, 4-amino-6-tert-butyl-3-methylthio-as-triazin-5-(4H)-one, 2,4-dichlorophenoxyacetic acid, its salts or esters, the s-triazines such as 2-methylthio-4,6-bis-(ethylamino)-s-triazine, aryl 4-nitrophenyl ethers such as 2,4,6-trichlorophenyl 4-nitrophenyl ether and 2,4-dichlorophenyl 4-nitrophenyl for ether for controlling a broad spectrum of weeds.

The agricultural chemicals listed above are exemplary of the compounds which can be mixed with the active compounds and are not intended to limit the invention in any way. Broadly speaking, the compounds of the invention are used at levels of about 0.1 to about 15 kilograms, preferably about 0.25 to about 10 per hectare The lower rates in this range will generally be selected on lighter soils, soils low in organic matter content, for selective weed control in crops, or in situations where maximum persistence is not necessary.

Herbicidal activity of compounds of this invention was discovered in greenhouse tests.

PROCEDURE TEST 1

Seeds of crabgrass (Digitaria spp.), barnyardgrass (*Echinochloa crusgalli*), wild oats (*Avena fatua*), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a non-phtotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatmwent.

Rating for compounds tested by this procedure are recorded in Table I. Plant response was response was expressed on a scale extending from 0 = no injury to 10 = complete kill. Letter symbols used had the following meanings: B = burn, and C = necrosis/chlorosis.

RESULTS OF TEST 1
POST EMERGENCE
| COMPOUND | RATE kg/ha | BUSH BEAN | COT-TON | MORN-ING GLORY | COCK-LEBUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|---|---|
| 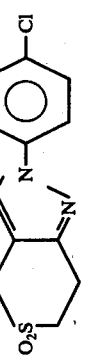 | 2/5 | 10B | 10B | 10B | 9B | 10B | 3B | 10B | 9B | 7B | 5B | 7B | 9B | 8B | 8B |
PRE-EMERGENCE
| COMPOUND | RATE Kg/ha | MORN-ING GLORY | COCK-LEBUR | CAS-SIA | NUT-SEDGE | CRAB-GRASS | BARN-YARD GRASS | WILD OATS | WHEAT | CORN | SOY-BEAN | RICE | SOR-GHUM |
|---|---|---|---|---|---|---|---|---|---|---|---|---|---|
| 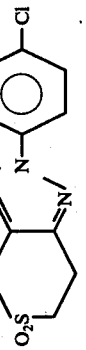 | 2/5 | 10C | 10C | 10C | 9C | 10C | 10C | 10C | 10C | 10C | 10C | 9C | 10C |

PROCEDURE TEST II

Two plastic bulb pans were filled with fertilized and limed Fallsington sandy loam soil. One pan was planted with corn, sorghum and several grassy weeds. The other pan was planted with soybeans, purple nutseedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter paper cup was also filled with prepared soil and planted with rice and wheat. Another 5-inch diameter paper cup was planted with sugarbeets. The above four containers were treated preemergence (compound sprayed on soil surface before seed germination).

Visual plant response ratings were made 28 days after treatment. The ratings were based on a scale extending from 0 = no injury, to 10 = complete kill. The symbol "H" denotes formative effects. The data are shown in the following table.

RESULTS TEST II

| COMPOUND | RATE Kg/Ha | Fallsington Sandy Loam | | | | | | | | | | |
|---|---|---|---|---|---|---|---|---|---|---|---|---|
| | | Crab-grass | Barn-yard-grass | Sor-ghum | Wild Oats | John-son-grass | Giant fox-tail | Ky. Blue-grass | Cheat-grass | Corn | Mustard | Cock-lebur |
| 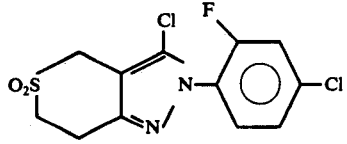 | 1/8 | 10H | 9H | 4H | 0 | 8H | 10H | 6H | 0 | 0 | 9H | 2H |
| | 1/2 | 10H | 9H | 9H | 5H | 7H | 10H | 10H | 6H | 6H | 10H | 7H |

| COMPOUND | RATE Kg/ha | Fallsington Sandy Loam | | | | | | | | | | |
|---|---|---|---|---|---|---|---|---|---|---|---|---|
| | | Pig-weed | Nut-sedge | H. In-digo | Morn-ing-glory | Cas-sia | Tea-weed | Vel-vet-leaf | Jim-son-weed | Soy-bean | Rice | Wheat | Su-gar-beets |
| 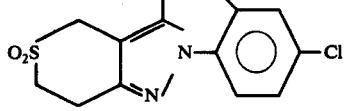 | 1/8 | 10H | 0 | 10H | 3H | 0 | 3H | 10H | 9H | 6H | 0 | 0 | 8H |
| | 1/2 | 10H | 2H | 10H | 10H | 10H | 10H | 10H | 10H | 7H | 7H | 4H | 10H |

PROCEDURE TEST II

Seeds of soybean, corn, cotton, rice, soybean, wheat, alfalfa, barnyardgrass (*Echinochloa crusgalli*), giant foxtail (*Setaria faberii*), morningglory (*Ipomoea hederacea*), nutsedge (*Cyperus rotundus*), crabgrass (*Digitaria sanguinalis*), wild oats (*Avena fatua*), velvetleaf (*Abutilon theophrasti*), sesbania (*Sesbania exaltate*), jimsonweed (*Datura stramonium*), and cocklebur (*Xanthium pennsylvanicum*) were planted in greenhouse soil and allowed to grow for 14 days. At this time, treatments were applied as "over-the-top" applications in a non-phytotoxic solvent containing a wetting agent.

Visual plant response ratings were made 14 days after treatment. The ratings were based on a scale extending from 0 = no injury, to 10 = complete kill. The symbol "B" denotes burn. The data are presented in the following table.

RESULTS TEST III
| COMPOUND | RATE Kg/Ha | Soybeans | Velvetleaf | Sesbania | Cassia | Cotton | Morning-glory | Alfalfa | Jimsonweed | Cocklebur | Corn | Crabgrass | Rice | Nutsedge | Barnyardgrass | Wheat | Giant Foxtail | Wild Oats | Sorghum |
|---|---|---|---|---|---|---|---|---|---|---|---|---|---|---|---|---|---|---|---|
| 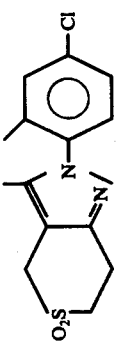 | 1/8 | 5B | 8B | 5B | 2B | 6B | 5B | 5B | 9B | 5B | 3B | 3B | — | 0 | 3B | 3B | 4B | 3B | 3B |
| | 1/2 | 6B | 9B | — | 6B | 9B | 7B | 6B | 10B | 7B | 3B | 6B | 0 | 0 | 4B | 4B | 7B | 4B | 4B |

I claim:
1. A compound of the formula

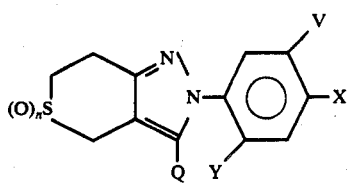

where
n is 0, 1, or 2;
Q is chlorine or bromine;
X is fluorine, chlorine, bromine, or cyano;
Y is hydrogen, fluorine, or chlorine; and
V is hydrogen, fluorine, chlorine or alkoxy of 1 to 3 carbon atoms.

2. A compound of claim 1 wherein n is 2.
3. A compound of claim 2 wherein Q is chlorine.
4. A compound of claim 2 wherein Y is fluorine.
5. A compound of claim 2 wherein V is hydrogen.
6. A compound of claim 2 wherein X is chlorine, bromine, or fluorine.
7. A compound of claim 1 wherein n is 2, Q is chlorine, Y is fluorine, V is hydrogen, and X is chlorine, bromine or fluorine.
8. The compound of claim 1, 3-chloro-2-(4-chloro-2-fluorophenyl)-2,4,6,7-tetrahydrothiopyranol[4,3-c]pyrazole-5,5-dioxide.
9. The compound of claim 1, 3-chloro-2-(4-bromo-2-fluorophenyl)-2,4,6,7-tetrahydrothiopyrano[4,3-c]pyrazole-5,5-dioxide.
10. A composition for the control of undesirable vegtation consisting essentially of a compound of claim 2 and at least one of (a) a surface-active agent and (b) a solid or liquid diluent.
11. A composition for the control of undesirable vegetation consisting essentially of a compound of claim 3 and at least one of (a) a surface-active agent and (b) a solid or liquid diluent.
12. A composition for the control of undesirable vegetation consisting essentially of a compound of claim 4 and at least one of (a) a surface-active agent and (b) a solid or liquid diluent.
13. A composition for the control of undesirable vegetation consisting essentially of a compound of claim 5 and at least one of (a) a surface-active agent and (b) a solid or liquid diluent.
14. A composition for the control of undesirable vegetation consisting essentially of a compound of claim 6 and at least one of (a) a surface-active agent and (b) a solid or liquid diluent.
15. A composition for the control of undesirable vegetation consisting essentially of a compound of claim 7 and at least one of (a) a surface-active agent and (b) a solid or liquid diluent.
16. A composition for the control of undesirable vegetation consisting essentially of the compound of claim 8 and at least one of (a) a surface-active agent and (b) a solid or liquid diluent.
17. A composition for the control of undesirable vegetation consisting essentially of the compound of claim 9 and at least one of (a) a surface-active agent and (b) a solid or liquid diluent.
18. A method for the control of undesirable vegetation comprising applying to the locus of such undesirable vegetation a herbicidally effective amount of a compound of claim 2.
19. A method for the control of undesirable vegetation comprising applying to the locus of such undesirable vegetation a herbicidally effective amount of a compound of claim 3.
20. A method for the control of undesirable vegetation comprising applying to the locus of such undesirable vegetation a herbicidally effective amount of a compound of claim 4.
21. A method for the control of undesirable vegetation comprising applying to the locus of such undesirable vegetation a herbicidally effective amount of a compound of claim 5.
22. A method for the control of undesirable vegetation comprising applying to the locus of such undesirable vegetation a herbicidally effective amount of a compound of claim 6.
23. A method for the control of undesirable vegetation comprising applying to the locus of such undesirable vegetation a herbicidally effective amount of a compound of claim 7.
24. A method for the control of undesirable vegetation comprising applying to the locus of such undesirable vegetation a herbicidally effective amount of the compound of claim 8.
25. A method for the control of undesirable vegetation comprising applying to the locus of such undesirable vegetation a herbicidally effective amount of the compound of claim 9.

* * * * *